United States Patent
Yao et al.

(10) Patent No.: US 8,001,843 B2
(45) Date of Patent: Aug. 23, 2011

(54) CIRCULAR ARC WIDE BEAM TRANSMISSION METHOD AND APPARATUS FOR ULTRASONIC IMAGING

(75) Inventors: Bin Yao, Shenzhen (CN); Qinjun Hu, Shenzhen (CN); Pengfei Yang, Shenzhen (CN); Bo Yang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 445 days.

(21) Appl. No.: 12/240,650

(22) Filed: Sep. 29, 2008

(65) Prior Publication Data

US 2009/0088644 A1 Apr. 2, 2009

(30) Foreign Application Priority Data

Sep. 29, 2007 (CN) .......................... 2007 1 0181051

(51) Int. Cl.
*G01N 29/00* (2006.01)
(52) U.S. Cl. ................. 73/609; 73/633; 73/640
(58) Field of Classification Search .............. 73/609, 73/616, 622–628, 633, 634, 637–640
See application file for complete search history.

(56) References Cited

U.S. PATENT DOCUMENTS

| 4,570,488 A | * | 2/1986 | Miwa et al. ............... 73/626 |
| 5,024,093 A | * | 6/1991 | Sasaki et al. ............. 73/633 |
| 5,460,178 A | * | 10/1995 | Hudon et al. ............. 600/443 |
| 5,583,292 A | * | 12/1996 | Karbach et al. ........... 73/638 |
| 5,585,565 A | * | 12/1996 | Glascock et al. .......... 73/644 |
| 5,638,821 A | | 6/1997 | Nakamura et al. |
| 5,669,384 A | * | 9/1997 | Park et al. ............... 600/447 |
| 6,192,006 B1 | * | 2/2001 | Iino et al. ............... 367/121 |
| 6,305,225 B1 | * | 10/2001 | Bae et al. ................ 73/602 |
| 6,957,583 B2 | * | 10/2005 | Tooma et al. ............. 73/625 |
| 7,516,664 B2 | * | 4/2009 | Meier et al. ............. 73/644 |
| 7,717,851 B2 | * | 5/2010 | Karasawa ............... 600/447 |

FOREIGN PATENT DOCUMENTS

| CN | 1286432 C | 11/2006 |
| CN | 1911177 A | 2/2007 |

\* cited by examiner

*Primary Examiner* — J M Saint Surin
(74) *Attorney, Agent, or Firm* — Kory D. Christensen; Stoel Rives LLP (57) ABSTRACT

A circular arc wide beam transmission method includes setting parameters for a focusing circular arc and calculating a transmission delay for each of the array elements in a transmission aperture of a probe based on the parameters for the focusing circular arc. An ultrasonic imaging system controls each array element to transmit ultrasonic waves according to the transmission delay for that array element.

13 Claims, 6 Drawing Sheets

CIRCULAR ARC WIDE BEAM TRANSMISSION METHOD AND APPARATUS FOR ULTRASONIC IMAGING

CROSS-REFERENCE TO RELATED APPLICATIONS

This application claims priority to Chinese Patent Application No. 200710181051.9, filed Sep. 29, 2007, for "CIRCULAR ARC WIDE BEAM TRANSMISSION METHOD AND APPARATUS FOR ULTRASONIC IMAGING," the disclosure of which is fully incorporated herein by reference.

TECHNICAL FIELD

The present disclosure relates generally to ultrasound imaging systems, and in particular, to a beam transmission method and apparatus used in ultrasound imaging.

BRIEF SUMMARY

A circular arc wide beam transmission method and apparatus for ultrasonic imaging is disclosed.

DETAILED DESCRIPTION

Conventionally, when a medical ultrasonic machine is used in imaging, a signal with a certain frequency and energy is employed to excite array elements in a probe to emit an ultrasonic beam. As the beam propagates into a tissue, the energy of the beam gradually becomes weak due to reflection and/or absorption. The reflected beam then travels back to the probe and is received by the array elements therein as echo information of the tissue. The information is then processed to form an ultrasonic image for display.

A conventional single beam technique usually demands a high lateral resolution. This requires the ultrasonic beam to be as narrow as possible and the beam energy be concentrated at the receiving location of a desired tissue, so that the echo information received is that of the desired tissue only without being disturbed by the information from other tissues. The beam is made the narrowest at the desired depth through transmission delays, resulting in a focused sound field. The single beam technique is advantageous in that it can achieve good image quality. But such technique cannot achieve very high frame rate, because the transmission times for a frame is equal to the number of beams in one frame. This limitation on frame rate has negative effect on clinical applications of certain technique that demand a high frame rate, e.g., the three-dimensional (3D) imaging.

One solution to improve frame rates is a multibeam technique which allows parallel reception of multiple scan lines for a single transmission of an ultrasonic beam. For multiple scan lines to be received in parallel, it is necessary for the target tissue area to be irradiated by multiple beams such that multiple echoes are generated. This requires that the transmit beams form a sound field capable of covering the tissue area such that it can reflect echoes the information of which will adequately represent an image of the target tissue area. Thus, a wider beam is needed as opposed to the narrow beam used in the single beam strong focusing technique. Further, in order for all the received beams to have even energy, the wide beam also needs to be comparatively flat.

Compared with the multibeam technique, the single beam strong focusing technique can achieve a better lateral resolution at the focus area, but it allows only one scan line to be received in each transmission. The multibeam technique has become an important research area driven by the need to improve frame rates. The principle of the multibeam technique is to allow for one transmission to receive multiple scan lines in parallel so that fewer transmissions are needed to form an image frame, thereby improving the frame rate. In the multibeam technique, as the received scan lines cover a larger area, if strong focusing is still employed as in the single beam technique, distortion will occur in the received scan lines due to uneveness of the energy of the sound field. To reduce distortion, wide beams are needed in this case so that the beams are wide enough to cover all the receive lines.

U.S. Pat. No. 6,585,648 discloses a method for transmitting a "fat" beam, in which multiple discrete transmitted waveforms are combined and launched as a single transmit event. The method is based on the fact that with the single beam technique, each discrete transmitted beam is actually composed of a superposition of component waveforms from many or all of the array elements, and only a single beam is launched for each scan-line. As such, it is possible to combine multiple waveforms (the combined waveform known as a "composite" waveform) transmitted from one array element and launch them as a single transmit event. The result of the transmission of such a waveform can be regarded as a superposition of the sound fields of multiple single beam transmissions.

U.S. Pat. No. 6,282,963 discloses a beam optimization method that obtains wide beams by optimizing the transmit apodization curves. According to the method, an optimal transmit apodization curve is obtained by establishing a mathematical model for the transmit beams, proposing several rules for evaluation of wide beams, and optimizing mathematical equations by optimization methods.

The methods disclosed in the abovementioned documents generate wide beams either by transmitting random waveforms (U.S. Pat. No. 6,585,648) or controlling the apodization curves (U.S. Pat. No. 6,282,963). However, because said methods are based on the prerequisite that the front-end of the ultrasonic system is capable of transmitting random waveforms, they cannot be applied in those ultrasonic machines that are only capable of transmitting unipolar-level or bipolar-level excited waveforms.

Additionally, the ultrasonic multibeam or fast imaging technique receives the ultrasonic information of a tissue area in a single transmission. What is obtained through conventional strong focusing transmission is point focusing beams, with focal point area being narrow and non-focal point area being wide. Since such a sound field cannot cover the whole target area, the ultrasonic information finally obtained will suffer from serious distortion.

The present disclosure provides a wide beam transmission method and apparatus to overcome the deficiencies in the prior art, wherein a single transmission can generate a sound field that covers the entire tissue area to be detected. According to a first aspect of the present disclosure, there is provided a circular arc wide beam transmission method for ultrasonic imaging. The method may include setting up parameters for a focusing circular arc, and calculating a transmission delay for each of the array elements in a transmission aperture of a probe based on the parameters for the focusing circular arc. In one embodiment, an ultrasonic imaging system controls each array element to transmit ultrasonic waves according to the transmission delay for that array element. The parameters for the focusing circular arc may include a location of the circle center, radius, and radian of the focusing circular arc, as well as a depth of focus.

The location of the circle center of the focusing circular arc may or may not coincide with the circle center of a circular arc of the probe surface. In one presently preferred embodiment, the center point of the focusing circular arc is located at the focal point of the transmission.

The calculation step may further comprise dividing the focusing circular arc into sub-focal points of equal radian, with each sub-focal point corresponding to an array element in the transmission aperture of the probe, whereby calculation of transmission delay for each array element is performed. The calculation of transmission delay may include calculating a respective distance between each array element and the corresponding sub-focal point, determining the maximum distance, calculating respective difference between the respective distance and the maximum distance, and dividing the respective difference by the sound velocity to obtain the transmission delay for each array element.

According to another aspect of the present disclosure, there is provided a circular arc wide beam transmission apparatus for ultrasonic imaging. The apparatus may include a setup module for setting up parameters for a focusing circular arc and a calculation module for calculating a transmission delay for each of the array elements in a transmission aperture of a probe based on the parameters for the focusing circular arc. In one embodiment, an ultrasonic imaging system controls each array element to transmit ultrasonic waves according to the transmission delay for that array element. The parameters for the focusing circular arc may include a location of the circle center, radius, and radian of the focusing circular arc, as well as a depth of focus.

In one presently preferred embodiment, the center point of the focusing circular arc is located at the focal point of the transmission. The calculation module may divide the focusing circular arc into sub-focal points with equal radian, with each sub-focal point corresponding to an array element in the transmission aperture of the probe, calculate a respective distance between each array element and the corresponding sub-focal point, determine the maximum distance, calculates respective difference between the respective distance and the maximum distance, and divide the respective difference by the sound velocity to obtain the transmission delay for each array element.

The method and apparatus of the present disclosure achieve wide beam transmission through weak focusing. By forming a circular arc curve at the focal point and applying a transmission delay for each array element in the transmission aperture, the sound beams emitted from the array elements do not focus at one point, thus obtaining a wide beam to cover the target area to be imaged. The method of the present disclosure employs a circular arc focusing and thus changes the method for calculating the transmission delay in strong focusing, whereby beams do not focus and wide beams are obtained.

The method has no particular requirement on the transmission waveforms and therefore can be carried out in most ultrasonic machines.

Figure 1:
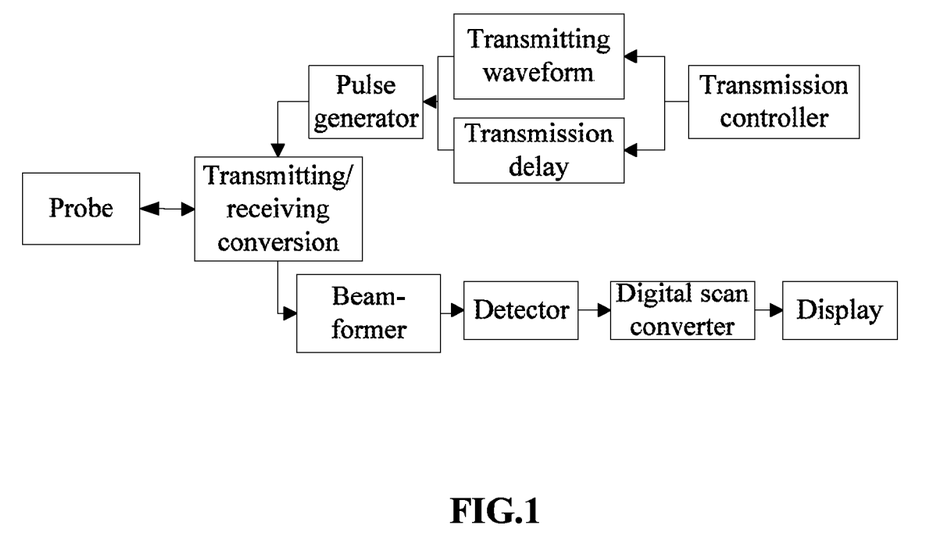
FIG. 1 shows a block diagram of an ultrasonic system.

FIG. 1 shows a block diagram of an ultrasonic system. The system includes a probe including a plurality of array elements, each array element being capable of mutual conversion between an electrical signal and a sound signal. The probe is connected to a transmitting/receiving conversion section. When the system is in a transmitting state, a transmission controller determines a transmitted waveform and a transmitting delay for each array element according to circumstances. A pulse generator then excites each array element in the probe according to the transmitted waveform and transmitting delay. The array elements then convert the electrical signals into sound signals and transmit them into the subject. When the system is in the receiving state, the array elements in the probe receive echoes from the subject, convert the echoes into electrical signals, and then transmit them back to the system, where they are further converted into digital signals by an AD converter. A beamformer is provided to synthesize the echoes received from each channel connected to an array element according to the delays to obtain modulated scan lines. A detector then processes the obtained signals by performing demodulation, envelope calculation, and sampling. The scan lines are processed by a digital scan converter (DSC) to form an ultrasonic image with rectangular coordinates capable of being displayed on a display device.

Figure 2:
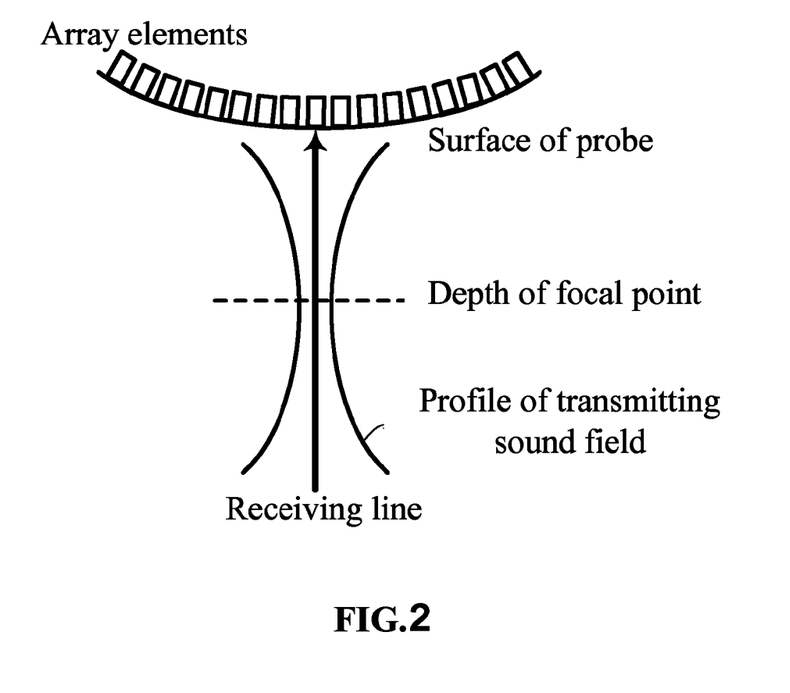
FIG. 2 shows a single beam transmitting and receiving.

FIG. 2 shows the transmitting and receiving of a single beam. As illustrated, the surface of the probe is in a circular arc shape, with a plurality of array elements evenly arranged thereon. Although seventeen array elements are shown, a skilled artisan will recognize that the actual number of array elements may vary from probe to probe. The transmission controller controls the waveform and delay for each array element, such that the ultrasonic wave is focused at the depth of the focal point. The transmitting sound field profile represents the whole shape and the major energy concentration area of the sound field. In the case of strong focusing for a single beam, the beam energy is relatively deconcentrated at the beginning and gradually becomes more concentrated up to its most concentrated and focused near the focal point, and then becomes deconcentrated again. The receive line of the sound field is at the middle of the sound field. Because the sound field is symmetrical and the received line is at the area where the energy is most concentrated, the receive line has low distortion.

Figure 3:
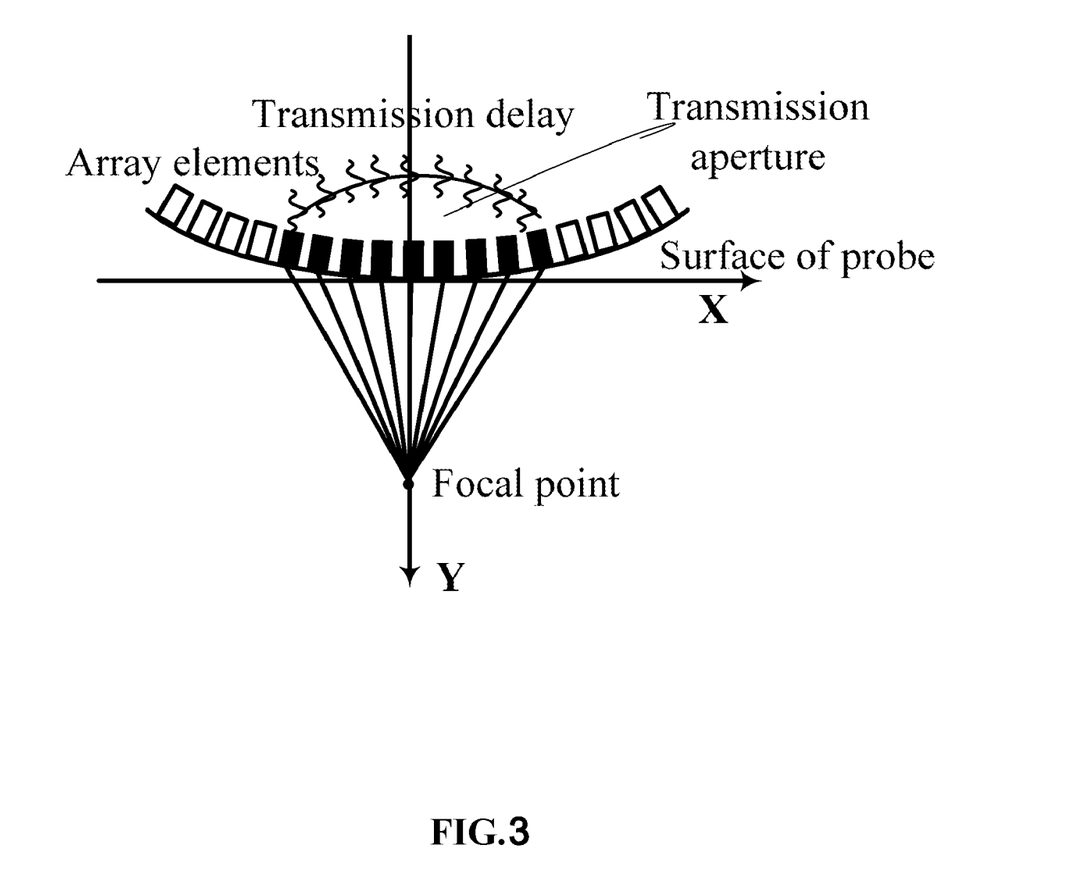
FIG. 3 is a schematic diagram showing a strong focusing transmission.

FIG. 3 is a schematic diagram showing a strong focusing transmission. Depending on the location of the target for transmission, the ultrasonic system selects a set of array elements to form a transmission aperture. As shown in FIG. 3, the array elements in black are those selected for transmission. The transmission controller controls the selection of the transmission aperture, and meanwhile calculates the delay and the waveform for each transmission. The delay is calculated based on a distance between an array element and the focal point. The purpose of setting a transmission delay is to enable the beam emitted from each of the array elements to reach the focal point at the same time so that the wave energy at the focal point area is most intensive. The result is that the sound field at that area is very narrow, thus improving lateral resolution at the focal point area. However, the sound field of such transmission is not even, i.e. there is a large difference between the energy distribution at the focal point and outside the focal point.

Referring to FIG. 3, a coordinate system with the central point of the transmission aperture as the origin is shown, with the X-axis being tangent to the surface of the probe and Y-axis being in the direction of the depth. The Y-axis passes the center of the circle since the surface of the convex array element of a probe is an arc. Given the transmission aperture {Ei}(i=1 ... K), where K is the number of the array element in the transmission aperture, the coordinates of each array element Ei (xi,yi), the coordinates of the focal point F ($x_F$, $y_F$), and given that strong focusing requires the sound waves emitted by all array elements to arrive at point F simultaneously, the following calculations can be made:

First, calculating the distance {$d_i$} between each array element and point F:

$$d_i = \sqrt{(x_i - x_F)^2 + (y_i - y_F)^2};$$

then, calculating the difference between each distance and the maximum distance:

$$\Delta d_i = \max(\{di\}) - di;$$

finally, calculating the delay $Delay_i$ for each array element Ei:

$$Delay_i = \Delta di/c;$$

where c is the sound velocity.

The transmission time delays as calculated above can compensate for the additional time resulting from the different distances between each array element and the focal point, such that the sound waves emitted from each of the array elements arrive at the focal point simultaneously. As sound waves are inphase superposed at the focal point, the energy at that point is much stronger than the energy at other locations at the same depth. Meanwhile, since not all sound waves are inphase superposed at other locations at the same depth, the sound field is narrower at the depth for the focal point than at other depths.

The single beam technique generally results in lower frame rates. Since an image frame is generally composed of several scan lines, if there are N (which is generally 128) array elements, and the scan line spacing is D (which is generally 1) times the array element spacing, then N/D=128 scan lines are needed to constitute a frame of image. In the case of single beam, M=128 transmissions are needed. If the depth to be detected is 30 cm, assuming the velocity of sound is 1540 m/s, then the time for a scan line to be received is equal to the time consumed by a sound wave to travel a 30 cm depth and return to the surface of the probe. As such, the time needed in obtaining a frame of image will be 30/100/1540*2*N/D≈0.05 seconds, i.e., a frame rate of about 20 frames/second. As seen from the calculation equation, it is possible to reduce the time to obtain a frame of image either by reducing the depth to be detected, increasing the scan line spacing D, or decreasing the transmission times N. However, reducing the depth to be detected is impractical, because such depth is determined by a doctor. Increasing scan line spacing D may be practicable, but this could lead to a deterioration of image quality for reduced information in a frame. Generally, a line spacing of one array element spacing is already quite big, and further increasing the scanning spacing will result in a poorer image quality.

Figure 4:
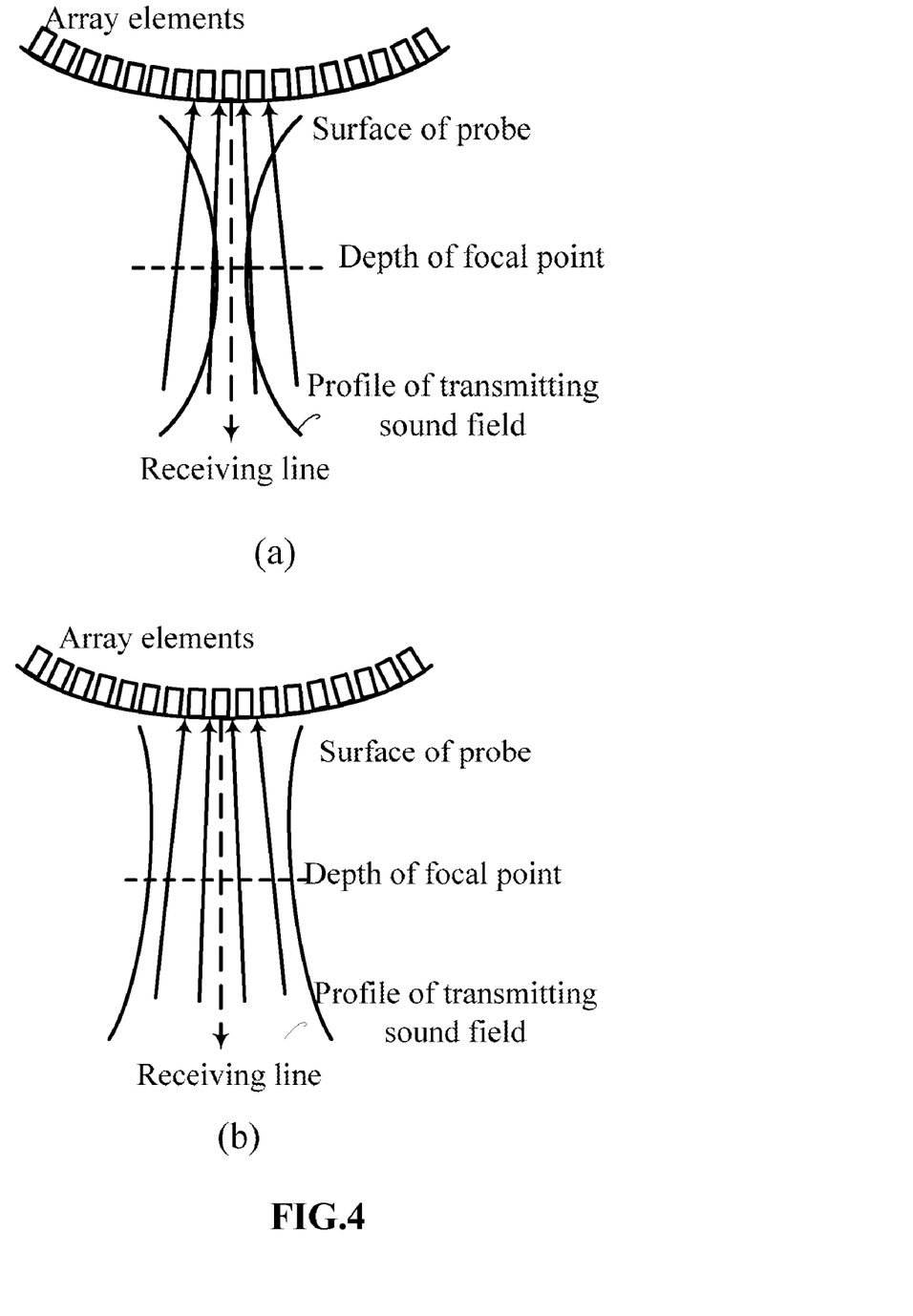
FIG. 4 is a schematic diagram showing multibeam receiving.

A method that uses a multibeam technique to improve the frame rate by decreasing the transmission times N is described with reference to FIG. 4. For each frame of image, if N is reduced by 4 times, the frame rate will be improved 4 times. The multibeam technique decreases the transmission times by allowing the parallel reception of scan lines from a plurality of locations in each transmission.

FIG. 4(a) shows a method having four beams, wherein the line spacing is 0.5 times of the array element spacing. Of course, this line spacing is exemplary only; in practice the line spacing is not necessarily limited to 0.5 times of the array element spacing. In fact, the multibeam technique is one that generates ultrasonic data of one tissue area in one transmit event. With the multibeam technique, a larger target area (a larger area usually means more receive beams) will result in a greater improvement of the frame rate.

As shown in FIG. 4(a), the probe has a convex array with an arc-shape surface. Each of the receiving lines is directed in the direction of the respective normal line of the surface of the probe. Thus, in the case of the multibeam, the tissue area covered is a sector instead of a rectangle, with the area of the far field being wide and that of the near field being narrow. This raises a higher requirement on the transmit sound field. FIG. 4(a) shows a sound field profile for strong focusing, from which it can be seen that not all receiving lines fall within the profile. This means that the energy of the ultrasonic beams fails to cover the entire area to be imaged, or the energy of the beams is not evenly distributed at different areas at the same depth. In other words, the energy at the portion covered by the ultrasonic sound field is high, and the energy at the portions not covered the ultrasonic sound field is low. As a result, energy distortion will occur to the final image. In consideration of the above problem, it is desired that transmit beams be wide enough so that the transmit sound field can cover the entire area, as shown in FIG. 4(b). According to the method of this embodiment, a wide beam transmission is realized by controlling transmission time delays. The beam width can be controlled so as to cover the width of the multibeam needing to be received.

Figure 5:
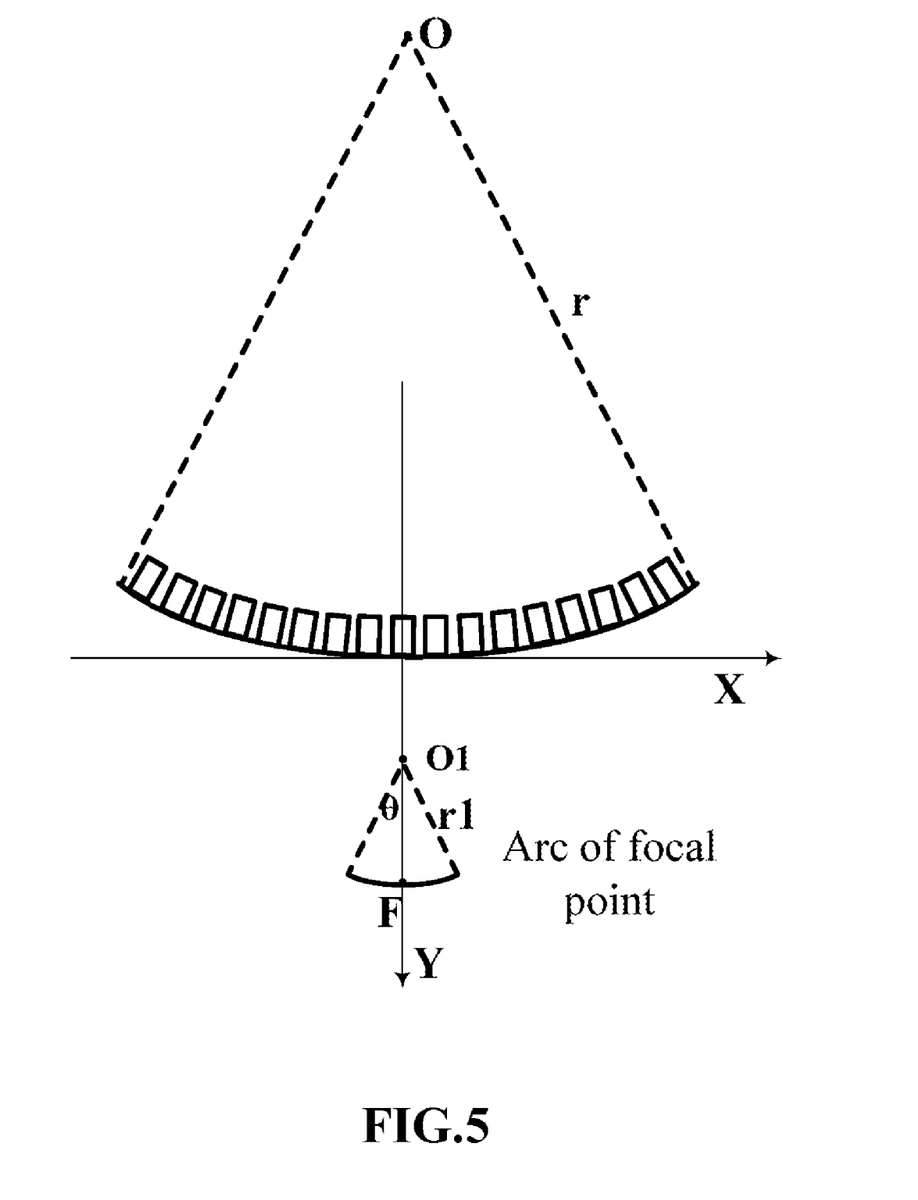
FIG. 5 shows a circular arc of the focal point in wide beam transmission

In strong focusing, beams are focused at a point because the transmission time delays are calculated based on the focal point. To obtain a wide beam, a method is needed to generate a beam which is not too divergent but sufficiently wide. As shown in FIG. 5, a circular arc focusing method is employed in this embodiment to control the width of the sound field. In FIG. 5, point O is the circle center of the circle defined by the circular arc surface of the probe and r is the radius thereof. If the focal point is at point F, the focal point can be extended to form a focusing circular arc passing point F, with the center of the circular arc at O1, the radius being r1 and the angle being θ, wherein the parameters of the focusing circular arc can be configured according to the desired beam width. In a particular example, O1 can be configured to coincide with O, then in that case the radius of the focusing circular arc will be r+Df, where Df is the depth of the focal point, and the angle may be configured according to the desired width of the sound beam.

Figure 7:
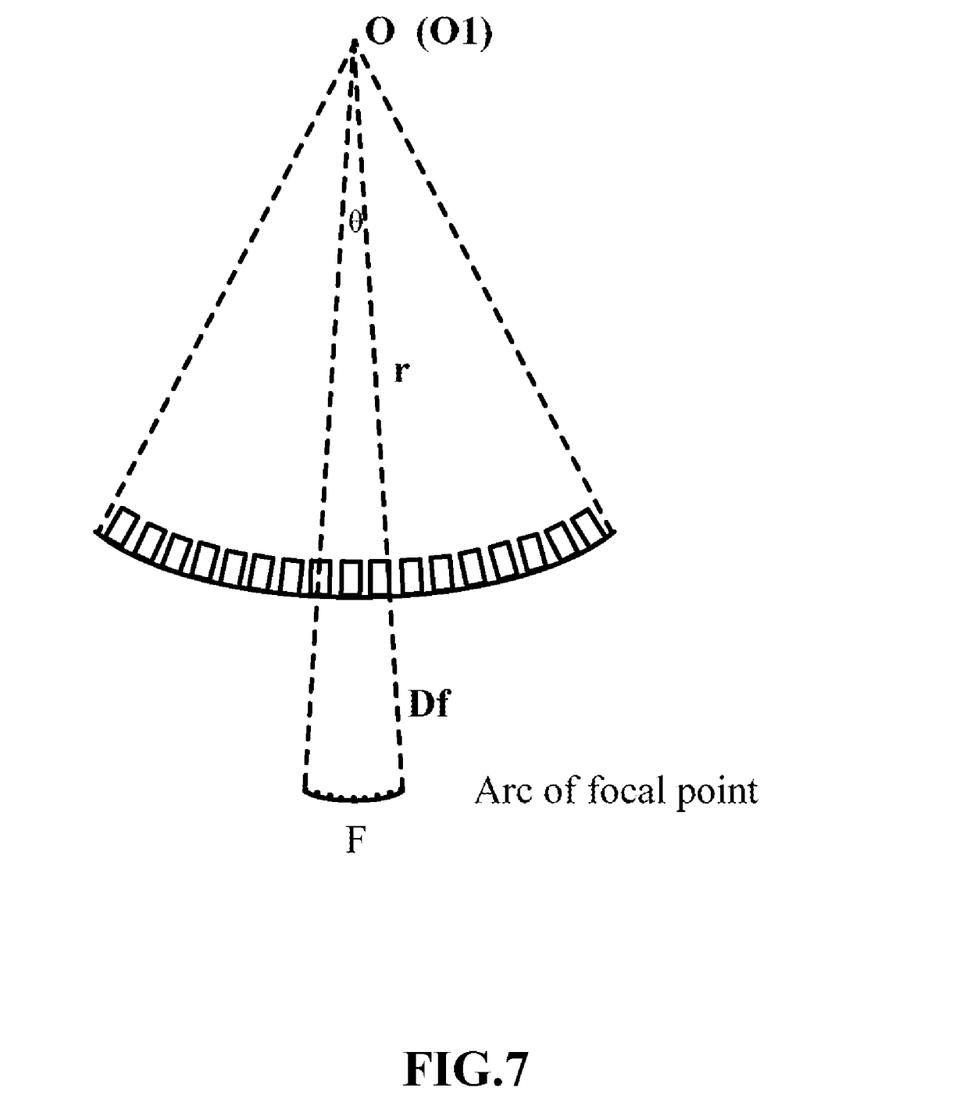
FIG. 7 is a diagram of circular arc focusing, with the arc of the focal point being concentric with the arc of a probe.

Referring to FIG. 7, in this example, transmission delay is calculated based on the condition where point O1 coincides with point O(xo,yo). As seen in FIG. 7, F is the focal point and Df is the depth of the focal point. The focal arc is a circular arc being concentric with the circular arc of the probe surface, so the radius of the focal arc is r+Df. Given the array element spacing pitch, the included angle Etheta between two adjacent array elements can be calcuated as follows:

$$Etheta = 2 \cdot a\sin(pitch/(2 \cdot r));$$

where the function a sin( ) is an inverse sinusoidal function. If the desired beam width is M (M is an integer) times of the array element spacing, then the needed included angle of the circular arc can be calcuated as follows:

$$\theta = (M-1) \cdot Etheta$$

In order to obtain a wide beam, the transmitting waveforms from each of the array elements should not focus in the area to be covered, but should have a certain width. Accordingly, the illustrated embodiment uses a focal circular arc which is divided into several sub-focal points, with each sub-focal point corresponding to a different array element. As the transmitting waveforms arrive at respective sub-focal points of the circular arc simultaneously and do not focus, no inphase superposition will take place during the propagation of such waveforms, thus resulting in a gradually diverged sound field. The beam width is indicative of the divergence state of the sound field at that location, and can be controlled by controlling the radian of focal arc. In this embodiment, an arc with an radian θ is divided into K points $\{\alpha_i\}$ (where, i=1 ... K) with equal radians, then it may be calculated through the equation that:

$$\alpha_i = -(\theta/2)+(i-1)\cdot(\theta/(K-1)) \quad \text{Eq. 1}$$

where i=1 ... K.

It is understood that $\alpha_i$ and $\alpha_K$ correspond respectively to the radian of the leftmost sub-focal point and that of the rightmost sub-focal point of the focal arc. Given the above information, the coordinates of the sub-focal point {Fi} can be calculated as follows:

$$\begin{cases} x_{Fi} = x_0 + (r+Df)\cdot \sin(\alpha_i) \\ y_{Fi} = y_0 + (r+Df)\cdot \cos(\alpha_i) \end{cases} \quad \text{Eq. 2}$$

where i=1 ... K.

Assuming that the array elements {Ei} (where, i=1 ... K) in the transmission aperture is also arranged from left to right, i.e. $x_1 <= x_2 <= \ldots <= x_K$, then a time delay can be calculated for each array element Ei such that the sound waves transmitted by the array elements can arrive at the corresponding sub-focal point $F_i$ at the same time. The calculation for the delay $\{Delay_i\}$ in this case is similar to that in strong focusing:

$$d_i = \sqrt{(x_i - x_{Fi})^2 + (y_i - y_{Fi})^2} \quad \text{Eq. 3}$$

$$\Delta d_i = \max(\{di\}) - di \quad \text{Eq. 4}$$

Finally, the time delay, $Delay_i$, for each array element Ei can be calculated:

$$Delay_i = \Delta d_i / c \quad \text{Eq. 5}$$

Figure 6:
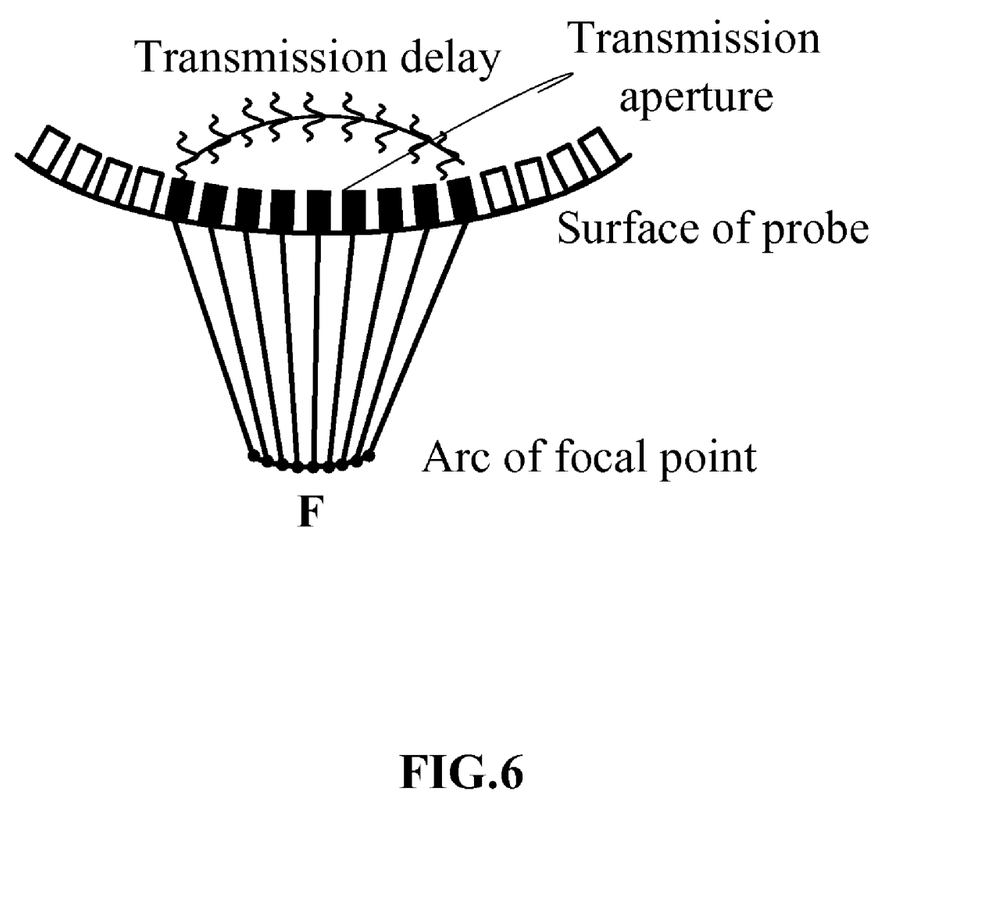
FIG. 6 shows a circular arc focusing in wide beam transmission.

Referring to FIG. 6, a focal arc instead of a focal point is used in this embodiment for calculating the transmission delay. Suppose the transmission aperture has K array elements, then the focal arc can be divided into K even sections, with each array element corresponding to one section, as shown in FIG. 6. The delay curve thus obtained is not a circular arc as in the case of strong focusing. In strong focusing, the beams can be focused at a focal point, so the inphase superposed focusing occurs at the focal point. But, since no focusing will take place in the whole process of propagation, the circular arc focusing used in this embodiment is a weak focusing, generating a wide beam.

The calculations given in the above example are based on the condition that the circle defined by the focal arc is concentric with that defined by the circular arc of the probe surface. When O and O1 do not coincide, similar calculations can also be made. With the case shown in FIG. 5, given the coordinates of O1, $[x_{o1},y_{o1}]$, the depth of the focal point, r1, and the angle θ, then the angle $\{\alpha_i\}$(where, i=1 ... K) of each sub-focal point in respect of O1 may be calculated using Equation 1, and then the coordinates of each sub-focal point can be calculated using the equation below:

$$\begin{cases} x_{Fi} = x_{o1} + r1\cdot \sin(\alpha_i) \\ y_{Fi} = y_{o1} + r1\cdot \cos(\alpha_i) \end{cases},$$

where i=1 ... K.

Finally, the same equations 3, 4 and 5 can be used for calculating the time delay for each array element.

According to the embodiments of the present disclosure, by controlling transmission time delays and implementing an arc focusing, a wide beam is obtained without increasing the cost. Through the use of arc focusing, sound beams are not focused at a point and is not too divergent, and the width of the transmit beam can be controlled as desired through the control of the parameters of the circular arc.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

What is claimed is:

1. A circular arc wide beam transmission method for ultrasonic imaging, comprising:
    setting parameters for a focusing circular arc of a single transmission of an ultrasonic beam from a transmission aperture of a probe; and
    calculating a transmission delay for each of a plurality of array elements in the transmission aperture of the probe based on the parameters for the focusing circular arc;
    wherein an ultrasonic imaging system controls each array element to transmit ultrasonic waves according to the calculated transmission delay for that array element.

2. The method according to claim 1, wherein the parameters for the focusing circular arc comprise a location of the circle center, radius, and radian of the focusing circular arc, as well as a depth of focus.

3. The method according to claim 2, wherein the location of the circle center of the focusing circular arc coincides with the circle center of a circular arc of the probe surface.

4. The method according to claim 2, wherein the location of the circle center of the focusing circular arc does not coincide with the circle center of a circular arc of the probe surface.

5. The method according to claim 1, wherein the center point of the focusing circular arc is located at the focal point of the transmission.

6. The method according to claim 1, wherein calculating further comprises dividing the focusing circular arc into sub-focal points with equal radian, with each sub-focal point corresponding to an array element in the transmission aperture of the probe, whereby calculation of transmission delay for each array element is performed.

7. The method according to claim 6, wherein the calculation of transmission delay includes calculating a respective distance between each array element and its corresponding sub-focal point, determining a maximum distance, calculating respective difference between the respective distance and the maximum distance, and dividing the respective difference by the sound velocity to obtain the transmission delay for each array element.

8. A circular arc wide beam transmission apparatus for ultrasonic imaging, comprising:
    a setting module for setting parameters for a focusing circular arc of a single transmission of an ultrasonic beam from a transmission aperture of a probe; and
    a calculation module for calculating a transmission delay for each of the array elements in the transmission aperture of the probe based on the parameters for the focusing circular arc;
    wherein an ultrasonic imaging system controls each array element to transmit ultrasonic waves according to the calculated transmission delay for that array element.

9. The apparatus according to claim 8, wherein the parameters for the focusing circular arc comprise a location of the circle center, radius, and radian of the focusing circular arc, as well as a depth of focus.

10. The apparatus according to claim 8, wherein the center point of the focusing circular arc is located at the focal point of the transmission.

11. The apparatus according to claim 8, wherein the calculation module divides the focusing circular arc into sub-focal points with equal radian, with each sub-focal point corresponding to an array element in the transmission aperture of the probe, calculates a respective distance between each array element and its corresponding sub-focal point, determines the maximum distance, calculates respective difference between the respective distance and the maximum distance, and divides the respective difference by the sound velocity to obtain the transmission delay for each array element.

12. A computer-readable medium comprising program code for performing a circular arc wide beam transmission method for ultrasonic imaging, the method comprising:
    setting parameters for a focusing circular arc of a single transmission of an ultrasonic beam from a transmission aperture of a probe; and
    calculating a transmission delay for each of a plurality of array elements in the transmission aperture of the probe based on the parameters for the focusing circular arc;
    wherein an ultrasonic imaging system controls each array element to transmit ultrasonic waves according to the calculated transmission delay for that array element.

13. A circular arc wide beam transmission apparatus for ultrasonic imaging, comprising:
    means for setting parameters for a focusing circular arc of a single transmission of an ultrasonic beam from a transmission aperture of a probe; and
    means for calculating a transmission delay for each of a plurality of array elements in the transmission aperture of the probe based on the parameters for the focusing circular arc;
    wherein an ultrasonic imaging system controls each array element to transmit ultrasonic waves according to the calculated transmission delay for that array element.

* * * * *